United States Patent
Hinterding et al.

(10) Patent No.: US 7,625,950 B2
(45) Date of Patent: *Dec. 1, 2009

(54) AMINO-PROPANOL DERIVATIVES AS SPHINGOSINE-1-PHOSPHATE RECEPTOR MODULATOR

(75) Inventors: Klaus Hinterding, Wittlingen (DE); Carsten Spanka, Lörrach (DE); Frédéric Zecri, Uffheim (FR)

(73) Assignee: Novartis AG, Basel (CH)

( * ) Notice: Subject to any disclaimer, the term of this patent is extended or adjusted under 35 U.S.C. 154(b) by 459 days.

This patent is subject to a terminal disclaimer.

(21) Appl. No.: 10/554,556

(22) PCT Filed: Apr. 29, 2004

(86) PCT No.: PCT/EP2004/004569

§ 371 (c)(1), (2), (4) Date: Oct. 26, 2005

(87) PCT Pub. No.: WO2004/096752

PCT Pub. Date: Nov. 11, 2004

(65) Prior Publication Data

US 2006/0211658 A1    Sep. 21, 2006

(30) Foreign Application Priority Data

Apr. 30, 2003 (GB) ................... 0309944.7
Dec. 19, 2003 (GB) ................... 0329500.3
Dec. 19, 2003 (GB) ................... 0329505.2

(51) Int. Cl.
*A01N 33/02* (2006.01)
*A61K 31/135* (2006.01)
*A01N 31/14* (2006.01)
*A61K 31/045* (2006.01)
*A01N 31/00* (2006.01)

(52) U.S. Cl. .......... 514/646; 514/717; 514/730
(58) Field of Classification Search ........... 514/772, 514/646, 717, 730
See application file for complete search history.

(56) References Cited

FOREIGN PATENT DOCUMENTS

| EP | 0 778 263 | 6/1997 |
|---|---|---|
| EP | 1 002 792 | 5/2000 |
| WO | 98/45259 | 10/1998 |
| WO | 02/076995 | 10/2002 |
| WO | 2004/024673 | 3/2004 |

OTHER PUBLICATIONS

Vessby et al., Cavedilol treatment of kidney graft recipients with chronic rejection. Clin. Transplantatiion 1999 13 484-490.*
Chemical Abstract 129:95608 and Japanese Patent No. 10147587, date Jun. 2, 1998.

* cited by examiner

*Primary Examiner*—Yong S Chong
(74) *Attorney, Agent, or Firm*—Hoxie & Associates LLC

(57) ABSTRACT

Compounds of formula (I)

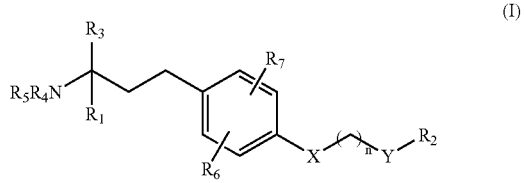

wherein $R_1$, $R_2$, $R_3$, $R_4$, $R_5$, $R_6$, $R_7$, X, Y and n are as defined in the specification, processes for their production, their uses and pharmaceutical compositions containing them.

8 Claims, No Drawings

AMINO-PROPANOL DERIVATIVES AS SPHINGOSINE-1-PHOSPHATE RECEPTOR MODULATOR

The present invention relates to amino-propanol derivatives, process for their production, their uses and pharmaceutical compositions containing them.

More particularly, the invention provides a compound of formula I

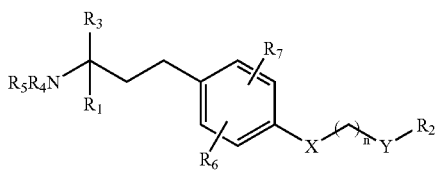

wherein $R_1$ is $C_{1-6}$alkyl; $C_{1-6}$alkyl substituted by hydroxy, $C_{1-2}$alkoxy or 1 to 6 fluorine atoms; $C_{2-6}$alkenyl; or $C_{2-6}$alkynyl;

each of X, Y independently is O, $CH_2$, or C=O;

$R_2$ is phenyl; naphthyl; $C_{3-6}$cycloalkyl; heteroaryl; a heterocyclic residue; phenyl$C_{1-2}$alkyl; $C_{3-6}$cycloalkyl$C_{1-2}$alkyl; heteroaryl$C_{1-2}$alkyl; heterocyclic$C_{1-2}$alkyl residue; wherein each may be ring-substituted by 1 to 5 substituents selected from hydroxy, halogen, $C_{1-4}$alkyl, $C_{1-4}$alkyl substituted by 1 to 5 fluorine atoms, $C_{3-6}$cycloalkyl, $C_{1-4}$alkoxy, $C_{1-4}$alkoxy substituted by 1 to 5 fluorine atoms, $C_{3-6}$cycloalkoxy, $C_{3-6}$cycloalkyl$C_{1-2}$alkyl, cyano, phenyl, and phenyl substituted by hydroxy, halogen, $C_{1-4}$alkyl, $C_{1-4}$alkyl substituted by 1 to 5 fluorine atoms, $C_{1-4}$alkoxy, $C_{1-4}$alkoxy substituted by 1 to 5 fluorine atoms, or cyano;

$R_3$ is $Z$—$X_2$ wherein Z is $CH_2$, CHF or $CF_2$ and $X_2$ is OH or a residue of formula (a)

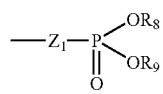

wherein $Z_1$ is a direct bond, $CH_2$, CHF, $CF_2$ or O, and each of $R_8$ and $R_9$, independently, is H or $C_{1-4}$alkyl optionally substituted by 1, 2 or 3 halogen atoms; and each of $R_4$ and $R_5$, independently, is H; $C_{1-4}$alkyl optionally substituted by 1, 2 or 3 halogen atoms; or acyl;

each of $R_6$ and $R_7$, independently, is H; hydroxy; halogen; $C_{1-4}$alkyl; $C_{1-6}$cycloalkyl; $C_{1-4}$alkoxy; $C_{1-6}$cycloalkoxy; $C_{3-6}$cycloalkyl$C_{1-2}$alkyl; or cyano; and n is 2 or 3;

in free form or in salt form.

Alkyl or alkyl moiety may be straight or branched chain. Alkenyl may be e.g. vinyl. Alkynyl may be e.g. propyn-2-yl. Acyl may be a residue R—CO wherein R is $C_{1-6}$alkyl, $C_{3-6}$cycloalkyl, phenyl or phenyl $C_{1-4}$-alkyl. Halogen may be fluorine, chlorine or bromine, preferably fluorine or chlorine. When alkyl is substituted by hydroxy, it is preferably on the terminal carbon atom. Phenyl$C_{1-2}$alkyl may be e.g. benzyl.

Heteroaryl may be a 5 to 8 membered aromatic ring comprising 1 to 4 heteroatoms selected from N, O and S, e.g. pyridyl, pyrimidinyl, pyrazinyl, furyl, oxazolyl, isoxazolyl, thienyl, thiazolyl, isothiazolyl, pyrrolyl, imidazolyl, or pyrazolyl.

By heterocyclic residue is meant a 3 to 8, preferably 5 to 8, membered saturated or unsaturated heterocyclic ring comprising 1 to 4 heteroatoms selected from N, O and S, e.g. tetrahydrofuryl, tetrahydropyranyl, aziridinyl, piperidinyl, pyrrolidinyl, piperazinyl. The heterocyclic residue may also be fused to an optionally substituted aryl or heteroaryl, e.g. phenyl, wherein Y is bound to said aryl or heteroaryl; examples include e.g. benzo[1,3]dioxolyl.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts. Compounds of formula I and their salts, in hydrate or solvate form are also part of the invention.

When the compounds of formula I have asymmetric centers in the molecule, various optical isomers are obtained. The present invention also encompasses enantiomers, racemates, diastereoisomers and mixtures thereof. For example, the central carbon atom bearing $R_1$, $R_3$ and $NR_4R_5$ may have the R or S configuration. Compounds having the following 3-dimensional configuration are generally preferred:

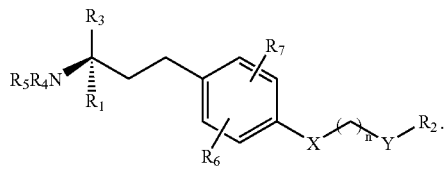

Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above, e.g. compounds of formula II, III or IV as indicated below.

In the compounds of formula I, the following significances are preferred individually or in any sub-combination:

1. X is O;
2. Y is O or S;
3. $R_1$ is $CH_3$ or $CH_2$—OH;
4. $R_2$ is phenyl; phenyl substituted by 1 or 2 substituents selected from halogen, $C_{1-2}$alkyl or $C_{1-2}$alkoxy; cyanophenyl; naphthyl; or benzo[1,3]dioxol-5-yl;
5. $R_3$ is $CH_2$—OH or $CH_2$—$OPO_3H_2$;
6. each of $R_4$ and $R_5$ is hydrogen;
7. $R_6$ is hydrogen, methoxy, methyl, or chloro; and
8. $R_7$ is hydrogen, methoxy, methyl, or chloro.

The present invention also includes a process for the preparation of a compound of formula I which process comprises a) for a compound of formula I wherein $R_3$ is $Z$—$X_2$, $X_2$ being OH, removing the protecting group present in a compound of formula II

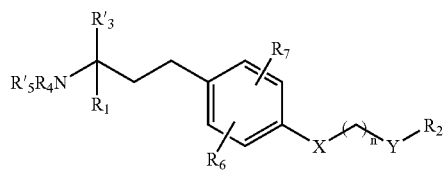

wherein X, n, $R_1$, $R_2$ and $R_4$ are as defined above, $R'_3$ is $Z$—$X_2$ wherein $X_2$ is OH and $R'_5$ is an amino protecting group, or b) for a compound of formula I wherein $R_3$ is $Z$—$X_2$, $X_2$ being a residue of formula (a), removing the protecting groups present in a compound of formula III

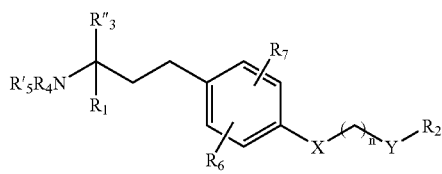

III wherein X, n, $R_1$, $R_2$, $R_4$ and $R'_5$ are as defined above, and $R''_3$ is $Z$—$X_2$ wherein $X_2$ is a residue of formula (a')

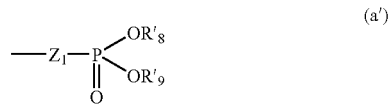

(a')

wherein $Z_1$ is as defined above and each of $R'_8$ or $R'_9$ is a hydrolysable or hydrogenolysable group or $R'_8$ and $R'_9$ form together a divalent bridging residue optionally fused to a ring (e.g. benzene ring), and, where required, converting the compounds of formula I obtained in free form into the desired salt form, or vice versa.

Process step a) may be carried out in accordance with methods known in the art. The removal of the amino protecting groups may conveniently be performed according to methods known in the art, e.g. by hydrolysis, e.g. in an acidic medium, for example using hydrochloric acid. Examples of protecting groups for amino groups are e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydropyranyl, trialkylsilyl, acyl, tert.-butoxy-carbonyl, benzyloxycarbonyl, 9-fluorenyl methoxy carbonyl, trifluoroacetyl, and the like.

In the residue of formula (a'), each of $R'_8$ and $R'_9$ may have the significance of e.g. tert-butyl, phenyl or benzyl or form together a cyclic system such as in 1,5-dihydro-2,4,3-benzodioxaphosphepin.

Process step b) may be performed according to methods known in the art, e.g. by hydrolysis, e.g. in a basic medium when $R'_6$ and $R'_7$ are each a hydrolysable group, for example using a hydroxide such as barium hydroxide or in an acidic medium when $R'_6$ and $R'_7$ are each a tert-butyl group. It may also be performed by hydrogenolysis, e.g. in the presence of a catalyst, e.g. Pd/C, followed by hydrolysis, e.g. in an acidic medium, for example HCl. Compounds of formulae II and III, used as starting materials, and salts thereof are also novel and form part of the invention.

The present invention also includes a process for the preparation of a compound of formula II which process comprises transforming a compound of formula IV

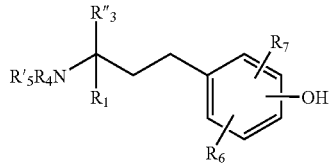

IV wherein $R_1$, $R'_3$, $R_4$ and $R'_5$ are as defined above, to introduce the desired residue —$(CH_2)_n$—Y—$R_2$ e.g. by an alkylation. Alkylation of the compounds of formula IV may be performed according to methods known in the art, e.g. by nucleophilic substitution, e.g. by reaction with an alkylating agent $R_2$—Y—$(CH_2)_n$—$X_3$ wherein $X_3$ is mesylate, tosylate, triflate, nosylate, chloride, bromide or iodide. The alkylation may also be carried out by following the Mitsunobu protocol using $R_2$—Y—$(CH_2)_n$—OH (e.g. as disclosed in Hughes, Organic Preparations and Procedures International 28, 127-64, 1996 or D. L. Hughes, Org. React. 42, 335, 1992), in solution or on solid phase support synthesis, e.g. by attaching the compound of formula IV to a resin. Alternatively, e.g. triphenylphosphine or diethyl azocarboxylate bound to a resin, e.g. polystyrene, may be used.

Compounds of formula III wherein $R'_8$ and $R'_9$ form a cyclic system, may be prepared as follows:

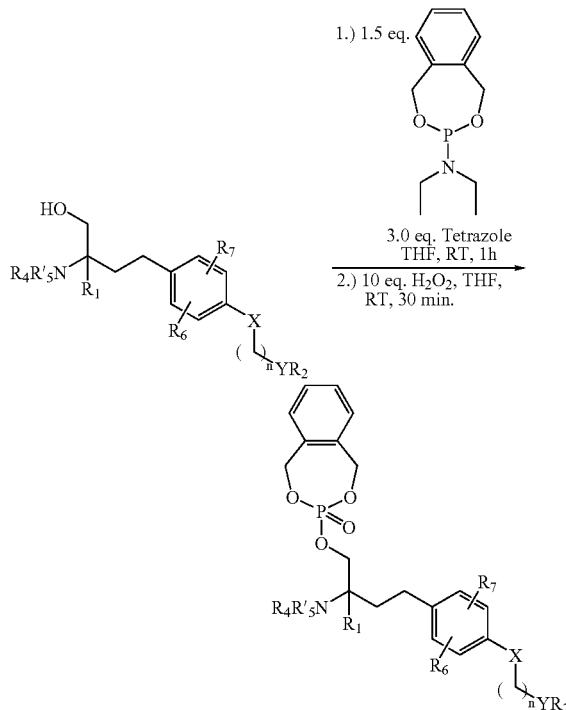

wherein X, Y, n, $R_1$, $R_2$, $R_4$ and $R'_5$ are as defined above.

Insofar as the production of the starting materials is not particularly described, the compounds are known or may be prepared analogously to methods known in the art or as disclosed in the Examples hereinafter.

The following Examples are illustrative of the invention. Melting points are uncorrected.

| | |
|---|---|
| RT = | room temperature |
| THF = | tetrahydrofuran |
| DMF = | dimethylformamide |
| MTBE = | methyl tert.-butyl ether |
| AcOEt = | ethyl acetate |

EXAMPLE 1

(R)-2-Amino-4-{4-[2-(4-chloro-phenoxy)-ethoxy]-phenyl}-2-methyl-butan-1-ol Hydrochloride To tert.-butyl (R-(3-{4-[2-(4-Chloro-phenoxy)-ethoxy]-phenyl}-1-hydroxymethyl-1-methyl-propylycarbamate (38 mg, 0.063 mmol) is added 4 M HCl in dry dioxane (1 mL). The clear colorless solution is stirred for 2 h protected from moisture. Then, the solution is evaporated to dryness and the partially crystalline residue is taken up in dry ether (5 mL). Sonication for 10 min gives a precipitate of colorless crystals. The product is filtered off, washed with cold ether (3×1 mL), and dried in vacuo to afford the title compound in form of a non hygroscopic colorless microcrystalline powder: HPLC: $t_R$=3.17 min., ESI+ MS: m/z=350/352 (MH$^+$).

tert.-butyl (R)-(3-{4-[2-(4-Chloro-phenoxy)-ethoxy]-phenyl}-1-hydroxymethyl-1-methyl-propyl)-carbamate may be prepared according to the following procedure:

To a solution of tert-butyl [(R)-1-hydroxy-4-(4-hydroxyphenyl)-2-methyl-but-2-yl]-carbamate (100 mg, 0.34 mmol) and 1-(2-bromoethoxy)-4-chlorobenzene (120 mg, 0.51 mmol, 1.5 eq.) in anhydrous DMF (2.5 mL) is added water free caesium carbonate (166 mg, 0.51 mmol, 1.5 eq.). The suspension obtained is stirred over night protected from moisture at 60° C. After cooling to RT the solids are filtered off and rinsed with DMF (2×1 mL). The combined filtrates are evaporated in a high vacuum to give a dark orange syrup. Purification by flash chromatography (FlashMaster II, MTBE/hexanes gradient 0% MTBE→40% MTBE within 45 min, then 40% MTBE 15 min) gives colorless crystals: HPLC: $t_R$=5.45 min., ESI+ MS: m/z=450/452.

By following the procedure of Example 1 but using the appropriate starting materials, the compounds of formula A, wherein $R_2$ and $R_6$ are as indicated in Table 1, may be prepared.

TABLE 1

A

| Example | $R_2$ | $R_6$ | M.S. Data |
|---|---|---|---|
| 2. | phenyl | H | MH$^+$ 316.5 |
| 3. | 3,5-dimethoxyphenyl | H | MH$^+$ 376.5 |
| 4. | 2-bromophenyl | H | MH$^+$ 394.3 |
| 5. | 2-methylphenyl | H | MH$^+$ 330.4 |
| 6. | 3-fluorophenyl | H | MH$^+$ 334.4 |
| 7. | 2,3-difluorophenyl | H | MH$^+$ 352.4 |
| 8. | 3-bromophenyl | H | MH$^+$ 394.3 |
| 9. | 4-chlorophenyl | methoxy | MH$^+$ 380.9 |
| 10. | phenyl | methoxy | MH$^+$ 346.5 |

EXAMPLE 11

2-Amino-4-{4-[2-phenoxy-ethoxy]-phenyl}-2-ethoxy-butan-1-ol Hydrochloride

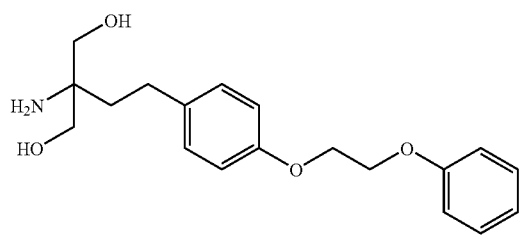

To a solution of 4-[2-(4-hydroxymethyl-2-methyl-4,5-dihydro-oxazol-4-yl)-ethyl]-phenol (300 mg, 1.27 mmol) in DMF (5 ml) was added $Cs_2CO_3$ (1.2 g, 3.83 mmol) and 2-phenoxyethyl bromide (770 mg, 1.27 mmol). The reaction mixture was stirred at 85° C. for 4 hours. AcOEt and water were then added, the organic layer was separated and the aqueous phase was extracted with AcOEt (3×50 ml). The combined organic extracts were washed with brine, dried over $MgSO_4$, and evaporated to dryness. Purification by flash chromatography (AcOEt/Hx 9:1) afforded (2-Methyl-4-{2-[4-(2-phenoxy-ethoxy)phenyl]-ethyl}-4,5-dihydro-oxazol-4-yl)-methanol as colorless oil. To a solution of (2-methyl-4-{2-[4-(2-phenoxy-ethoxy)phenyl]-ethyl}-4,5-dihydro-oxazol-4-yl)-methanol (50 mg, 0.14 mmol) in ethanol (2 ml) was added conc. HCl (2 ml). The reaction mixture was stirred at 85° C. for 2 hours, then concentrated to dryness. The residue was re-dissolved in AcOEt and precipitated with hexanes. The solid was filtered off, washed with dry ether and dried in vacuo to afford 2-amino-4-{4-[2-phenoxy-ethoxy]-phenyl}-2-ethoxy-butan-1-ol hydrochloride as a colorless powder. ESI+MS: m/z=332.3 (M+H)$^+$.

By following the procedure of Example 11 but using the appropriate starting materials, the compounds of formula B, wherein $R_2$ is as indicated in Table 2, may be prepared.

TABLE 2

B

| Example | $R_2$ | M.S. Data |
|---|---|---|
| 12 | 4-Br-phenyl | (M + H)$^+$ 410.1 |
| 13 | 2-Br-phenyl | (M + H)$^+$ 410.1 |
| 14 | naphthyl | (M + H)$^+$ 382.2 |
| 15 | 3-MeO-phenyl | (M + H)$^+$ 362.2 |
| 16 | 3-EtO-phenyl | (M + H)$^+$ 376.0 |
| 17 | 2-Cl-phenyl | (M + H)$^+$ 366.2 |
| 18 | 2-Me-phenyl | (M + H)$^+$ 346.2 |
| 19 | 2-MeO-phenyl | (M + H)$^+$ 362.2 |
| 20 | 4-MeO-phenyl | (M + H)$^+$ 362.0 |
| 21 | 2,4-diCl-phenyl | (M + H)$^+$ 400.1 |
| 22 | benzo[1,3]dioxol-5-yl | (M + H)$^+$ 376.0 |
| 23 | 2-CN-phenyl | (M + H)$^+$ 357.4 |

TABLE 2-continued

B

| Example | R₂ | M.S. Data |
|---|---|---|
| 24 | 3-Me-phenyl | MH⁺ 346.4 |
| 25 | 3-F-phenyl | MH⁺ 350.4 |

EXAMPLE 26

(+/−) Mono-(2-Amino-4-{4-[2-phenoxy-ethoxy]-phenyl}-2-ethoxy-butan)

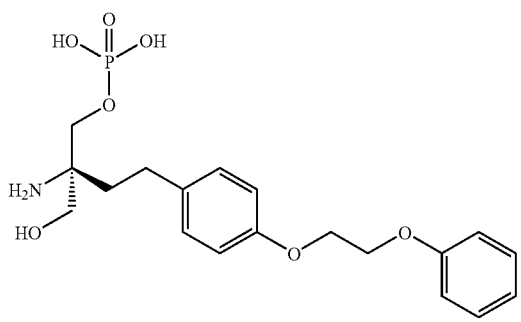

To a solution of (2-methyl-4-{2-[4-(2-phenoxy-ethoxy)-phenyl]-ethyl}-4,5-dihydro-oxazol-4-yl)-methanol (200 mg, 0.56 mmol) and tetrazole (197 mg, 2.81 mmol, 5 eq., recrystallized from toluene) in dry THF (5 ml) was added di-tert-butyl-N,N-diisopropylphosphoramide (561 mg, 2.25 mmol, 4 eq.). After stirring under argon at RT for 3 h, $H_2O_2$ (30%, 10 eq.) was slowly added at 0° C. with vigorous stirring. The reaction mixture was stirred for further 30 min, followed by addition of saturated sodium thiosulfate solution (5 ml). The organic layer was separated and the aqueous phase was extracted with ether (3×20 ml). The combined organic extracts were washed with brine, dried over $MgSO_4$, and evaporated to dryness. Purification by flash chromatography (AcOEt/hexane 1:1) afforded phosphoric acid di-tert-butyl ester 2-methyl-4-{2-[4-(2-phenoxy-ethoxy)-phenyl]-ethyl}-4,5-dihydro-oxazol-4-ylmethyl ester as colorles crystals. Finally, to a solution of phosphoric acid di-tert-butyl ester 2-methyl-4-{2-[4-(2-phenoxy-ethoxy)-phenyl]-ethyl}-4,5-dihydro-oxazol-4-ylmethyl ester (150 mg, 0.27 mmol) in ethanol (5 ml) was added conc. HCl (5 ml). The reaction mixture was stirred at 50° C. for 2 hours, then concentrated to dryness. The residue was re-dissolved in AcOEt and precipitated with hexanes. The solid was filtered off, washed with dry ether and dried in vacuo to afford mono-(2-amino-4-{4-[2-phenoxy-ethoxy]-phenyl}-2-ethoxy-butan) phosphate as a colorless powder. ESI+ MS: m/z=410.2 (M−H)⁺.

By following the procedure of Example 26 but using the appropriate starting materials, the compounds of formula C, wherein $R_2$ is as indicated in Table 3, may be prepared.

TABLE 3

C

| Example | R₂ | M.S. Data |
|---|---|---|
| 27 | 4-Br-phenyl | (M + H)⁺ 488.0, (M − H)⁺ 490.0 |
| 28 | 2-Br-phenyl | (M + H)⁺ 488.0, (M − H)⁺ 490.0 |
| 29 | 3-OMe-phenyl | (M + H)⁺ 440.2 |
| 30 | 3-OEt-phenyl | (M + H)⁺ 440.2 |
| 31 | 2-Cl-phenyl | (M + H)⁺ 444.0 |
| 32 | 2-Me-phenyl | (M + H)⁺ 424.0 |
| 33 | 3-Me-phenyl | MH⁺ 426.4 |

TABLE 3-continued

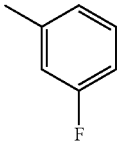

| Example | R$_2$ | M.S. Data |
|---|---|---|
| 34 | 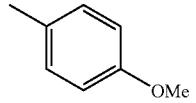 | MH$^+$ 430.3 |
| 35 | 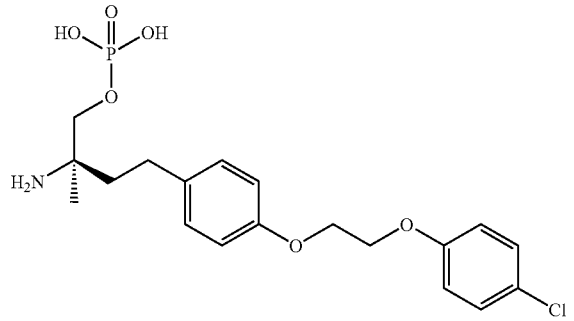 | (M + H)$^+$ 442.4 |

EXAMPLE 36

(R)-Mono-(2-amino-4-{4-[2-(4-chloro-phenoxy)-ethoxy]-phenyl}-2-methyl-butyl) phosphate

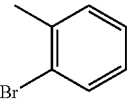

tert.-butyl [3-{4-[2-(4-Chloro-phenoxy)-ethoxy]-phenyl}-1-(di-tert-butoxy-phosphoryloxy-methyl)-1-methyl-propyl]-carbamate (44 mg, 0.069 mmol) was dissolved in 4 M HCl in dioxane (2 mL). After stirring for 2 h the slightly turbid solution was evaporated. The colorless semi-solid residue was sonicated with dry ether (5 mL) to give a colorless precipitate. The solid was filtered off, washed with dry ether and vacuum dried to afford a off white powder: HPLC: t$_R$=3.11 min., ESI+ MS: m/z=430/432 (M–H$^+$).

tert.-butyl [3-{4-[2-(4-Chloro-phenoxy)-ethoxy]-phenyl}-1-(di-tert-butoxy-phosphoryloxy-methyl)-1-methyl-propyl]-carbamate be prepared according to the following procedure:

To a solution of tert.-butyl (R)-(3-{4-[2-(4-Chloro-phenoxy)-ethoxy]-phenyl}-1-hydroxymethyl-1-methyl-propyl)-carbamate (40 mg, 0.089 mmol, Ex. 1a) and tetrazole (19 mg, 0.27 mmol, 3 eq., recrystallized from toluene) in dry THF (1 mL) was added di-tert.-butyl N,N-diethyl-phosphoramidite (36 μL, 0.13 mmol, 1.5 eq.). The reaction mixture was stirred under argon at RT for 2 h. Then, H$_2$O$_2$ (30%, 91 μL, 0.89 mmol, 10 eq.) was injected at 0° C. with vigorous stirring. The reaction mixture was stirred for further 30 min, followed by addition of saturated sodium thiosulfate solution (1 mL). The organic layer was separated and the aqueous phase was extracted with ether (3×1 mL). The combined organic extracts were washed with brine, dried over MgSO$_4$, and evaporated to dryness. The crude material was purified by flash chromatography (FlashMaster II, MTBE/hexanes gradient 0% MTBE→50% MTBE within 45 min, then 50% MTBE 15 min) to afford colorless crystals: HPLC: t$_R$=6.64 min., ESI+ MS: m/z=642/644 (MH$^+$).

By following the procedure of Example 36 but using the appropriate starting materials, the compounds of formula D, wherein R$_2$ and R$_6$ are as indicated in Table 4, may be prepared.

TABLE 4

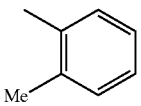

| Example | R$_2$ | R$_6$ | M.S. Data |
|---|---|---|---|
| 38 | phenyl | H | (M + H)$^+$ 396.3 |
| 39 | 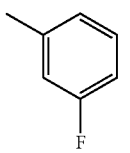 | H | MH$^+$ 472.0 |
| 40 | 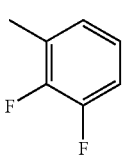 | H | MH$^+$ 408.2 |
| 41 | (3-F-phenyl) | H | MH$^+$ 412.1 |
| 42 | (2,3-diF-phenyl) | H | MH$^+$ 432.1 |
| 43 | phenyl | methoxy | M – H 424.4 |

EXAMPLE 44

2-Amino-2-{2-[4-(3-phenoxy-propoxy)-phenyl]-ethyl}-propane-1,3-diol Hydrochloride

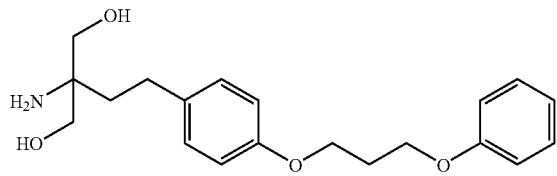

To a solution of 4-[2-(4-hydroxymethyl-2-methyl-4,5-dihydro-oxazol-4-yl)-ethyl]-phenol (300 mg, 1.27 mmol) in DMF (5 ml) was added $Cs_2CO_3$ (1.2 g, 3.83 mmol) and (3-bromo-propoxy)-benzene (273 mg, 1.27 mmol). The reaction mixture was stirred at 85° C. for 4 hours. AcOEt and water were then added, the organic layer was separated and the aqueous phase was extracted with AcOEt (3×50 ml). The combined organic extracts were washed with brine, dried over $MgSO_4$, and evaporated to dryness. Purification by flash chromatography (AcOEt/Hexane 9:1) affords (2-methyl-4-{2-[4-(3-phenoxy-propoxy)-phenyl]-ethyl}-4,5-dihydro-oxazol-4-yl)-methanol as colorless oil. To a solution of (2-methyl-4-{2-[4-(3-phenoxy-propoxy)-phenyl]-ethyl}-4,5-dihydro-oxazol-4-yl)-methanol (50 mg, 0.135 mmol) in ethanol (2 ml) was added conc. HCl (2 ml). The reaction mixture was stirred at 85° C. for 2 hours, then concentrated to dryness. The residue was re-dissolved in AcOEt and precipitated with hexanes. The solid was filtered off, washed with dry ether and dried in vacuo to afford 2-amino-2-{2-[4-(3-phenoxy-propoxy)-phenyl]-ethyl}-propane-1,3-diol hydrochloride as a colorless powder. ESI+ MS: m/z=370.4 (M+H)$^+$.

By following the procedure of Example 44 but using the appropriate starting materials, the compounds of formula E, wherein $R_2$ and Y are as indicated in Table 5, may be prepared.

TABLE 5

E

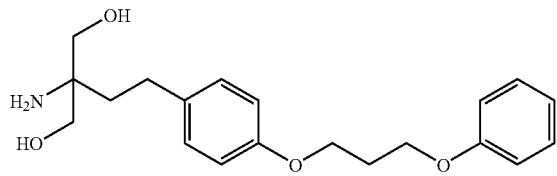

| Example | $R_2$ | Y | M.S. Data |
|---|---|---|---|
| 45 | 3-MeO-phenyl | O | (M + H)$^+$ 376.4 |
| 46 | 2-Br-phenyl | O | (M + H)$^+$ 425.3 |
| 47 | 4-Cl-phenyl | O | (M + H)$^+$ 380.9 |
| 48 | OMe / Br (substituted phenyl) | O | (M + H)$^+$ 455.3 |
| 49 | 3-Me-phenyl | O | (M + H)$^+$ 360.4 |
| 50 | 4-MeO-phenyl | O | (M + H)$^+$ 376.4 |
| 51 | phenyl | S | (M + H)$^+$ 362.5 |

EXAMPLE 52

((R)-2-Amino-2-methyl-4-[4-(3-phenoxy-propoxy) phenyl]-butan-1-ol Hydrochloride

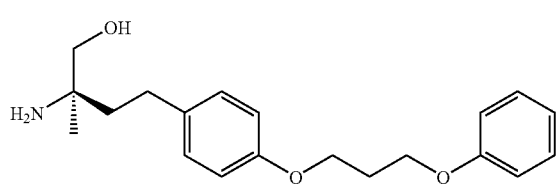

To {(R)-1-Hydroxymethyl-1-methyl-3-[4-(3-phenoxy-propoxy)-phenyl]-propyl}-carbamic acid tert-butyl (50 mg, 0.11 mmol) was added 4 M HCl in dry dioxane (1 mL). The clear colorless solution was stirred for 2 h protected from moisture. Then, the solution was evaporated to dryness and the partially crystalline residue was taken up in dry ether (5 mL). Sonication for 10 min gives a precipitate of colorless crystals. The product was filtered off, washed with cold ether (3×1 mL), and dried in vacuo to afford the title compound in form of a non hygroscopic colorless microcrystalline powder. ESI+MS: m/z=330.4 (MH$^+$).

{(R)-1-Hydroxymethyl-1-methyl-3-[4-(3-phenoxy-propoxy)-phenyl]-propyl}-carbamic acid tert-butyl may be prepared according to the following procedure:

To a solution of tert-butyl [(R)-1-hydroxy-4-(4-hydroxyphenyl)-2-methyl-but-2-yl]-carbamate (100 mg, 0.34 mmol) and (3-bromo-propoxy)-benzene (109.6 mg, 0.51 mmol, 1.5 eq.) in anhydrous DMF (2.5 mL) was added water free cesium carbonate (166 mg, 0.51 mmol, 1.5 eq.). The suspension obtained was stirred over night protected from moisture at 60° C. After cooling to RT the solids were filtered off and rinsed with DMF (2×1 mL). The combined filtrates were evaporated in a high vacuum to give a dark orange syrup. Purification by flash chromatography (FlashMaster II, MTBE/hexanes gradient 0% MTBE→40% MTBE within 45 min, then 40% MTBE 15 min) gave colorless crystals: ESI+MS: m/z=430.4.

EXAMPLE 53

(R)-2-Amino-4-{4-[3-(5-bromo-2-methoxy-phenoxy)-propoxy]-phenyl}-2-methyl-butan-1-ol Hydrochloride

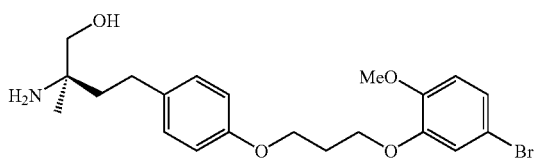

The title compound was prepared as described in example 52 using 4-bromo-2-(3-bromo propoxy)-1-methoxy-benzene instead of (3-bromo-propoxy)-benzene. ESI+ MS: m/z=439.3 (M+H)$^+$.

EXAMPLE 54

(+/−) Mono Phosphoric acid mono-{2-amino-2-hydroxymethyl-4-[4-(3-phenoxy-propoxy)-phenyl]-butyl} ester

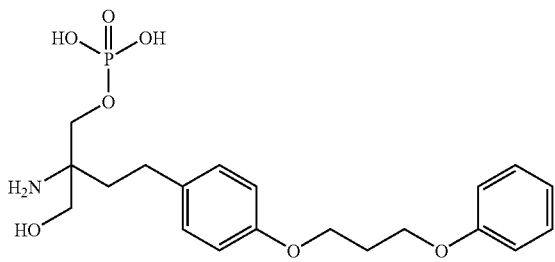

To a solution of (2-methyl-4-{2-[4-(3-phenoxy-propoxy)-phenyl]-ethyl}-4,5-dihydro-oxazol-4-yl)-methanol (200 mg, 0.54 mmol) and tetrazole (189 mg, 2.70 mmol, 5 eq., recrystallized from toluene) in dry THF (5 ml) was added di-tert-butyl-N,N-diisopropylphosphoramide (538.5 mg, 2.16 mmol, 4 eq.). After stirring under argon at RT for 3 h, $H_2O_2$ (30%, 10 eq.) was slowly added at 0° C. with vigorous stirring. The reaction mixture was stirred for further 30 min, followed by addition of saturated sodium thiosulfate solution (5 ml). The organic layer was separated and the aqueous phase was extracted with ether (3×20 ml). The combined organic extracts were washed with brine, dried over $MgSO_4$, and evaporated to dryness. Purification by flash chromatography (AcOEt/hexane 1:1) affords (+/−) phosphoric acid di-tert-butyl ester 2-methyl-4-{2-[4-(3-phenoxy-propoxy)-phenyl]-ethyl}-4,5-dihydro-oxazol-4-ylmethyl ester as colorless crystals. Finally, to a solution of phosphoric acid di-tert-butyl ester 2-methyl-4-{2-[4-(3-phenoxy-propoxy)-phenyl]-ethyl}-4,5-dihydro-oxazol-4-yl-methyl ester (50 mg, 0.089 mmol) in ethanol (5 ml) was added conc. HCl (5 ml). The reaction mixture was stirred at 50° C. for 2 hours, then concentrated to dryness. The residue was re-dissolved in AcOEt and precipitated with hexanes. The solid was filtered off, washed with dry ether and dried in vacuo to afford (+/−) mono phosphoric acid mono-{2-amino-2-hydroxymethyl-4-[4-(3-phenoxy-propoxy)phenyl]-butyl} ester as a colorless powder. ESI+MS: m/z=426.4 (M−H)+.

By following the procedure of Example 54 but using the appropriate starting materials, the compounds of formula F, wherein $R_2$, $R_{10}$ and Y are as indicated in Table 6, may be prepared.

TABLE 6

F

| Example | $R_2$ | $R_{10}$ | Y | M.S. Data |
|---|---|---|---|---|
| 55 | 2-Br-phenyl | $CH_2$—OH | O | (M + H)+ 505.3 |
| 56 | OMe, Br-dimethylphenyl | $CH_2$—OH | O | (M + H)+ 535.3 |
| 57 | phenyl | $CH_2$—OH | S | (M + H)+ 442.4 |
| 58 | OMe, Br-dimethylphenyl | $CH_3$ | O | (M + H)+ 519.3 |

The compounds of formula I in free form or in pharmaceutically acceptable salt form, exhibit valuable pharmacological properties, e.g. lymphocyte recirculation modulating properties, e.g. as indicated in in vitro and in vivo tests and are therefore indicated for therapy.

A. In Vitro

The compounds of formula I have binding affinity to individual human SIP receptors as determined in following assays:

Sphingosine-1-Phosphate (S1P) Receptor Profiling

Agonist activities of compounds are tested on the human SIP receptors EDG-1 ($S1P_1$), EDG-3 ($S1P_3$), EDG-5 ($S1P_2$), EDG-6 ($S1P_4$) and EDG-8 ($S1P_5$). Functional receptor activation is assessed by quantifying compound induced GTP [$\gamma$-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised SIP receptor expressing membrane protein (10-20 μg/well) in the presence of 50 mM Hepes, 100 mM NaCl, 10 mM $MgCl_2$, 10 μM GDP, 0.1% fat free BSA and 0.2 nM GTP [$\gamma$-$^{35}$S] (1200 Ci/mmol). After incubation in 96 well microtiterplates at RT for 120 min, unbound GTP [$\gamma$-$^{35}$S] is separated by a centrifugation step. Luminescence of SPA beads triggered by membrane bound GTP [$\gamma$-$^{35}$S] is quantified with a TOP count plate reader (Packard). $EC_{50}$s are calculated using standard curve fitting software. In this assay, the compounds of formula I have a binding affinity to $S1P_1$ receptor <50 nM.

| Example | S1P$_1$ EC$_{50}$ [nM] | S1P$_3$ EC$_{50}$ [nM] | S1P$_4$ EC$_{50}$ [nM] | S1P$_5$ EC$_{50}$ [nM] |
|---|---|---|---|---|
| 36 | 0.6 Agon. | 15 Agon. | >1000 | 14 Agon. |
| 38 | 8.6 Agon. | >1000 | 28 Agon. | 11.7 Agon. |
| 42 | 5.5 Agon. | >1000 | 8.2 Agon. | 6.3 Agon. |
| 43 | 8 Agon. | 340 Agon. | 43 Agon. | 0.5 Agon. |
| 56 | 8.5 Agon. | >10000 Agon. | 1.6 Agon. | 16.5 Agon |

Agon. = agonist

B. In Vivo: Blood Lymphocyte Depletion

A compound of formula I or the vehicle is administered orally by gavage to rats. Tail blood for hematological monitoring is obtained on day −1 to give the baseline individual values, and at 2, 6, 24, 48 and 72 hours after application. In this assay, the compounds of formula I deplete peripheral blood lymphocytes when administered at a dose of 0.03 to 3 mg/kg. For example, following results are obtained: depletion of peripheral blood lymphocytes by more than 50%

| | |
|---|---|
| Example 1: | 0.03 mg/kg p.o. after 6 h, 0.02 mg/kg p.o. after 24 h. |
| Example 3: | 0.01 mg/kg p.o. after 6 h, <0.03 mg/kg p.o. after 48 h. |
| Example 7: | 0.03 mg/kg p.o. after 6 h, 0.02 mg/kg p.o. after 48 h. |
| Example 9: | 0.2 mg/kg p.o. after 6 h, >1 mg/kg p.o. after 48 h. |
| Example 53: | 0.1 mg/kg p.o. after 6 h, 0.5 mg/kg p.o. after 48 h. |

The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveits, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, angiogenesis, Alzheimer's disease, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 0.1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A, FK 506 or $ISA_{TX}247$; a mTOR inhibitor, e.g. rapamycin, 40-O-(2-hydroxyethyl)-rapamycin, CCI779, ABT578, AP23573, AP23464, AP23675, AP23841, TAFA-93, biolimus 7 or biolimus 9; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

Where the compounds of formula I are administered in conjunction with other immuno-suppressive/immunomodulatory, anti-inflammatory. chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:
1. A compound of formula I

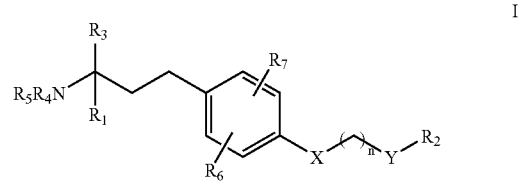

wherein
$R_1$ is $C_{1-6}$alkyl; $C_{1-6}$alkyl substituted by hydroxy, $C_{1-2}$alkoxy or 1 to 6 fluorine atoms; $C_{2-6}$alkenyl; or $C_{2-6}$alkynyl;
X is O;
Y is O;
$R_2$ is phenyl; naphthyl; $C_{3-6}$cycloalkyl; heteroaryl; a heterocyclic residue; phenyl-$C_{1-2}$alkyl; $C_{3-6}$cycloalkylC$_{1-2}$alkyl; heteroarylC$_{1-2}$alkyl; heterocyclic-C$_{1-2}$alkyl residue; wherein each may be ring-substituted by 1 to 5 substituents selected from hydroxy, halogen, $C_{1-4}$alkyl, $C_{1-4}$alkyl substituted by 1 to 5 fluorine atoms, $C_{3-6}$cycloalkyl, $C_{1-4}$alkoxy, $C_{1-4}$alkoxy substituted by 1 to 5 fluorine atoms, $C_{3-6}$cycloalkoxy, $C_{3-6}$cycloalkylC$_{1-2}$alkyl, cyano, phenyl, and phenyl substituted by hydroxy, halogen, $C_{1-4}$alkyl, $C_{1-4}$alkyl substituted by 1 to 5 fluorine atoms, $C_{1-4}$alkoxy, $C_{1-4}$alkoxy substituted by 1 to 5 fluorine atoms, or cyano, and where heteroaryl is a 5-to-8-membered aromatic ring comprising 1-to-4 heteroatoms selected from N, O and S, and heterocyclic is a 3-to-8-membered saturated heterocyclic ring comprising 1-to-4 heteroatoms selected from O, N and S, which ring may be fused to a phenyl;
$R_3$ is Z—$X_2$ wherein Z is $CH_2$, $CF_2$ or $CF_2$ and $X_2$ is OH or a residue of formula (a)

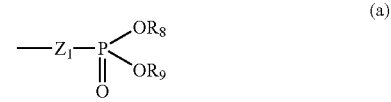

wherein $Z_1$ is a direct bond, $CH_2$, CHF, $CF_2$ or O, and each of $R_8$ and $R_9$, independently, is H or $C_{1-4}$alkyl optionally substituted by 1, 2 or 3 halogen atoms; and
each of $R_4$ and $R_5$, independently, is H; $C_{1-4}$alkyl optionally substituted by 1, 2 or 3 halogen atoms; or R—CO, where R is $C_{1-6}$-alkyl, $C_{3-6}$-cycloalkyl, phenyl or phenyl-$C_{1-4}$-alkyl;
each of $R_6$ and $R_7$, independently, is H; hydroxy; halogen; $C_{1-4}$alkyl; $C_{1-6}$cycloalkyl; $C_{1-4}$alkoxy; $C_{3-6}$-cycloalkoxy; $C_{3-6}$cycloalkylC$_{1-2}$alkyl; or cyano; and
n is 2 or 3;
in free form or in salt form.

2. A compound of formula I wherein $R_2$ is phenyl; phenyl substituted by 1 or 2 halogen, $C_{1-2}$alkyl or $C_{1-2}$alkoxy; cyanophenyl; naphthyl; or benzo[1,3]dioxol-5-yl, in free form or in salt form.

3. A compound according to claim 1 wherein each of $R_6$ and $R_7$, independently, is hydrogen, methoxy, methyl, or chloro in free form or in salt form.

4. A compound according to claim 1 wherein $R_3$ is $CH_2$—OH or $CH_2$—$OPO_3H_2$.

5. A pharmaceutical composition comprising a compound according to claim 1, or a pharmaceutically acceptable salt thereof in association with a pharmaceutically acceptable diluent or carrier therefore.

6. A pharmaceutical combination comprising a compound according to claim 1, in free form or in pharmaceutically acceptable salt form, and at least one co-agent.

7. A compound according to claim 1 wherein $R_1$ is $CH_3$ or $CH_2$—OH.

8. A compound according to claim 1 wherein each of $R_4$ and $R_5$ is hydrogen.

* * * * *

UNITED STATES PATENT AND TRADEMARK OFFICE
CERTIFICATE OF CORRECTION

PATENT NO.        : 7,625,950 B2
APPLICATION NO.   : 10/554556
DATED             : December 1, 2009
INVENTOR(S)       : Hinterding et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 804 days.

Signed and Sealed this

Second Day of November, 2010

David J. Kappos
*Director of the United States Patent and Trademark Office*